US005667484A

United States Patent [19]

Brossard

[11] Patent Number: 5,667,484

[45] Date of Patent: Sep. 16, 1997

[54] METHOD FOR CONTROLLING THE REFLEX RESPONSE OF THE MUSCLES OF A LIVING BODY JOINT

[76] Inventor: André Brossard, 4053 Barn Street, Rosemère, Québec, Canada, J7A 1Z4

[21] Appl. No.: 426,667

[22] Filed: Apr. 21, 1995

[51] Int. Cl.[6] .......... A61F 13/00

[52] U.S. Cl. .......... 602/21; 602/64; 606/201

[58] Field of Search .......... 128/735, 907, 128/744; 602/20, 26; 604/201, 204

[56] References Cited

U.S. PATENT DOCUMENTS

| | | | |
|---|---|---|---|
| Re. 15,446 | 9/1922 | Hamilton . | |
| 3,515,125 | 6/1970 | Ruskin | 128/744 X |
| 3,934,583 | 1/1976 | Hollingshead et al. . | |
| 4,085,756 | 4/1978 | Castiglia . | |
| 4,133,311 | 1/1979 | Karczewski . | |
| 4,309,991 | 1/1982 | DeMarco . | |
| 4,323,232 | 4/1982 | Terpening . | |
| 4,367,733 | 1/1983 | Stromgren . | |
| 4,369,775 | 1/1983 | Gamm . | |
| 4,409,976 | 10/1983 | Pence . | |
| 4,441,493 | 4/1984 | Nirschl . | |
| 4,475,542 | 10/1984 | Brossard . | |
| 4,597,395 | 7/1986 | Barlow et al. . | |
| 4,693,241 | 9/1987 | Trznadel . | |
| 4,702,234 | 10/1987 | Huntjens . | |
| 4,777,946 | 10/1988 | Watanabe et al. . | |
| 4,787,381 | 11/1988 | Hubbard et al. . | |
| 4,926,848 | 5/1990 | Shimkus et al. . | |
| 4,949,957 | 8/1990 | Cucchiara . | |
| 5,099,860 | 3/1992 | Amrein . | |
| 5,160,314 | 11/1992 | Peters . | |

FOREIGN PATENT DOCUMENTS

| | | |
|---|---|---|
| 9415540 | 7/1994 | WIPO . |

OTHER PUBLICATIONS

"Reflex Actions on the γ-Muscle-Spindle Systems of Muscles Acting at the Knee Joint Elicited by Stretch of the Posterior Cruciate Ligament" H. Johannson et al. Neuro-Orthopedics (1989) pp. 16–20.

*Primary Examiner*—Richard J. Apley
*Assistant Examiner*—Kim M. Lee

[57] ABSTRACT

To control the reflex response of a muscle or muscular group articulating a joint of a living body, the method and device apply an external pressure to the mechano-receptors guiding the natural reflex mechanism of the muscle or muscular group. The mechano-receptors include skin mechano-receptors and deeper joint mechano-receptors. To increase the reflex response of the muscle or muscular group, a light pressure intensity≦200 mmHg is applied to stimulate only the skin mechano-receptors and thereby increase the reflex response of the muscle or muscular group. To inhibit the reflex response of the muscle or muscular group, a high pressure intensity≧400 mmHg is applied to stimulate the deeper joint mechano-receptors such as the Golgi tendons to thereby increase the reflex response of the muscle or muscular group.

2 Claims, 10 Drawing Sheets

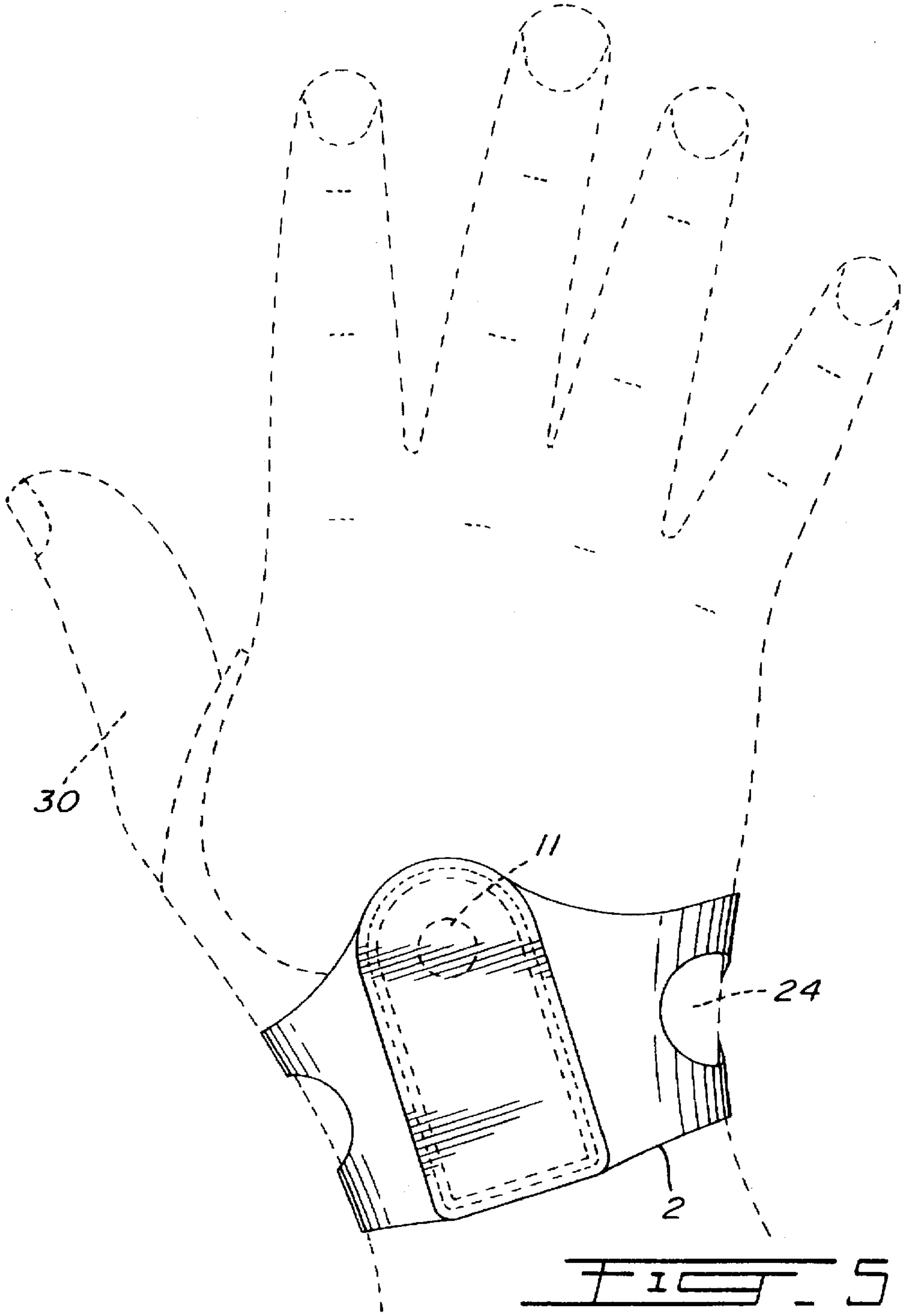
FIG. 5
FIG. 6
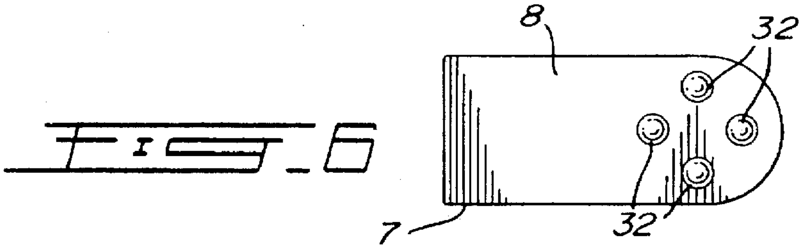

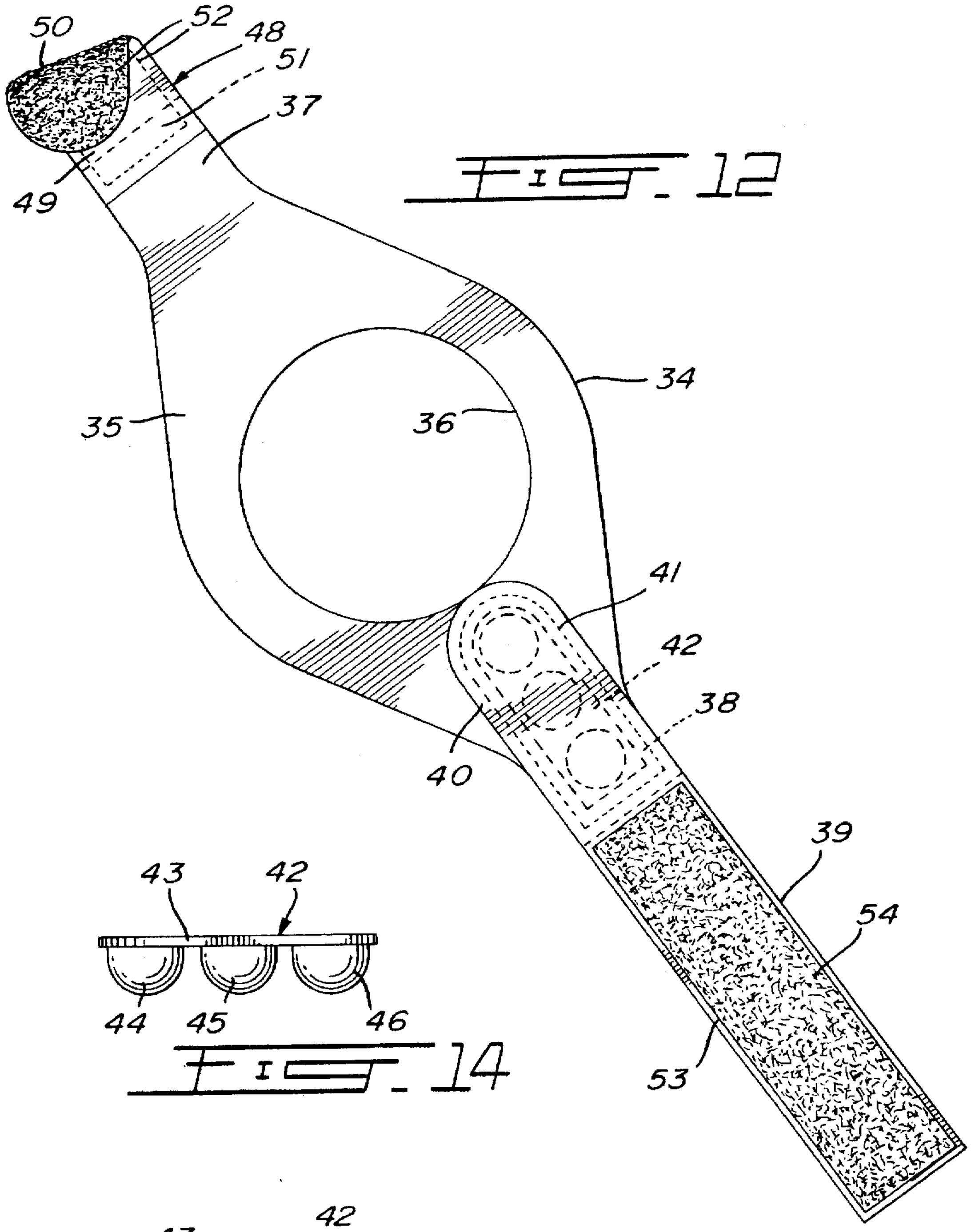
FIG. 12
FIG. 14
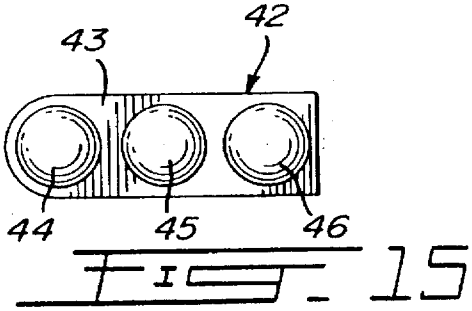
FIG. 15

METHOD FOR CONTROLLING THE REFLEX RESPONSE OF THE MUSCLES OF A LIVING BODY JOINT

BACKGROUND OF THE INVENTION

1. Field of the invention:

The present invention relates to a method and device using a specific mechanical stimulation (external pressure) to control the reflex response of a muscle or muscular group articulating a living body joint.

2. Brief description of the prior art:

Repetition motion syndromes are often met in individuals having one or many joints or muscles which are oversolicited. For example, when an individual uses to stand on one and the same leg, the articulated joints and/or muscles associated to this legs are likely to suffer from repetitive motion syndromes. As another example, a sportsman or a worker repeating the same movements oversolicites given body joints and muscles which are therefore subject to suffer from repetitive motion syndromes.

Obviously, the most direct method of reducing the probability of repetitive motion syndromes is to reduce the work load and/or to decrease the number or repetitions of a given movement. However, this solution is not available either at work and in sport situations.

Another method of prevention is to protect the overactive joint and muscle-tendon complex associated therewith externally, using for example orthotics and/or taping.

A further method is to increase the efficiency of the muscles surrounding an articulated joint, in particular through exercise.

OBJECT OF THE INVENTION

An object of the present invention is to use a specific mechanical stimulation (SMS) at an articulated body joint to increase the reflex response and therefore the efficiency of the muscle(s) associated to this joint and, hence, to prevent these joint and muscle(s) from being oversolicited and therefore to prevent these joint and muscle(s) from suffering from repetitive motion syndromes.

Another object of the subject invention is to provide a method and device capable by means of a SMS to inhibit the reflex response of a given muscle or muscular group to rest or relax this muscle or muscular group subjected, for example, to spasms.

SUMMARY OF THE INVENTION

More particularly, in accordance with the present invention, there is provided a method of controlling the reflex response of a muscle or muscular group articulating a joint of a living body, the living body comprising mechano-receptors guiding a natural reflex mechanism of the muscle or muscular group. This method is characterized in that it comprises the step of applying an external pressure to the mechano-receptors, this pressure applying step comprising the step of submitting the mechno-receptors to a pressure intensity adequate to increase or inhibit the reflex response of the muscle or muscular group.

In accordance with preferred embodiments:

the mechano-receptors comprise skin mechno-receptors, and the submitting step comprises producing a light pressure intensity $\leqq$200 mmHg for stimulating only the skin mechano-receptors and thereby increasing the reflex response of the muscle or muscular group;

the mechano-receptors comprise deeper joint mechno-receptors, and the submitting step comprises producing a high pressure intensity $\geqq$400 mmHg for stimulating the deeper joint mechano-receptors and thereby inhibiting the reflex response of the muscle or muscular group;

the joint mechano-receptors comprise at least one Golgi tendon of the muscle or muscular group, and the pressure applying step comprises applying the external pressure to the Golgi tendon;

the joint of the living body is a wrist joint, and the pressure applying step comprises applying the external pressure to the area of the dorsal radiocarpal ligament;

the joint of the living body is an ankle joint, and the pressure applying step comprises applying the external pressure to the area of the calcaneofibular ligament, lateral talocalcaneal ligament, and interosseous talocalcaneal ligament; and the joint of the living body comprises a lumbar spine, and the pressure applying step comprises applying the external pressure to the area of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, and piriformis ligaments.

The present invention also relates to a device for controlling the reflex response of a muscle or muscular group articulating a joint of a living body, the living body comprising mechano-receptors guiding a natural reflex mechanism of the muscle or muscular group. The device is characterized in that it comprises means for applying an external pressure to the mechano-receptors, the pressure applying means comprising means for submitting the mechano-receptors to a pressure intensity adequate to increase or inhibit the reflex response of the muscle or muscular group.

When the joint of the living body is a wrist joint, the pressure applying means may comprise an elastic wrist band and a pressure-applying protuberance mounted on the wrist band to apply the external pressure to the area of the dorsal radiocarpal ligament.

When the joint of the living body is an ankle joint, the pressure applying means may comprise an elastic ankle band and at least one pressure-applying protuberance mounted on the ankle band to apply the external pressure to the area of the calcaneofibular ligament, lateral talocalcaneal ligament, and interosseous talocalcaneal ligament.

When the joint of the living body comprises a lumbar spine, the pressure-applying means comprises elastic shorts formed with an insert-receiving pocket, and a generally flat insert mounted in the pocket of the elastic shorts and formed with a plurality of pressure-applying protuberances to apply the external pressure to the area of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, and piriformis ligaments.

The objects, advantages and other features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 5 is a top plan view of a human wrist and hand wearing the elastic wrist band of FIG. 2;

FIG. 6 is a bottom plan view of a second embodiment of insert to be mounted in the pocket of the elastic wrist band of FIG. 2, this insert being formed with a set of four pressure-applying protuberances;

FIG. 12 illustrates an elastic ankle band comprising pressure-applying protuberances for applying an external pressure (SMS) to the area of the calcaneofibular ligament, lateral talocalcaneal ligament, and interosseous talocalcaneal ligament;

FIG. 14 is a side elevational view of an insert to be mounted in a pocket of the ankle band of FIG. 12, this insert being formed with a series of three pressure-applying protuberances for applying an external pressure (SMS) to the area of the calcaneofibular ligament, lateral talocalcaneal ligament, and interosseous talocalcaneal ligament, respectively;

FIG. 15 is a bottom plan view of the insert of FIG. 14;

DETAILED DESCRIPTION OF THE PREFERRED EMBODIMENT

Experimentation was conducted on the wrist joint of many human subjects. More specifically, ten university students were tested on a Kincom dynamometer for maximum isometric and concentric force (30°/sec, 3 trials) of four wrist movements, namely pronation (from −30° to 20°), supination (from −30° to 20°), flexion (from −20° to 20°) and extension (from −20° to 20°), and that for two conditions: with and without specific mechanical stimulation (SMS). Standard surface electromyography (EMG) of the flexor carpi radialis and extensor carpi ulnaris was also monitored. Isometric contractions were further measured for normalization purposes.

Specific mechanical stimulation (SMS) was applied in the form of a pressure on the dorsal aspect of the wrist at the level of the capitate bone. More specifically, pressure was applied to the area 1 (FIG. 1) of the dorsal radiocarpal ligament by a small piece of high density foam material maintained on the area 1 of interest by means of an elastic wrist band.

Figure 2:
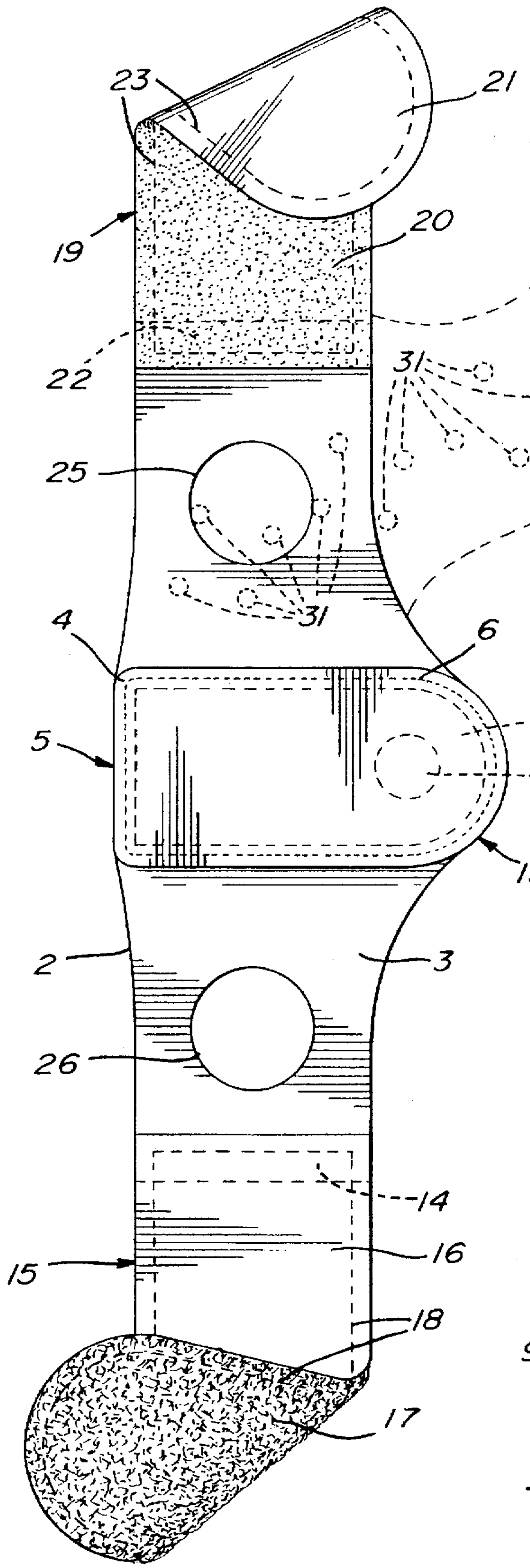
FIG. 2 illustrates an elastic wrist band comprising a pressure-applying protuberance for applying an external pressure (SMS) to the area of the dorsal radiocarpal ligament.

An example of elastic wrist band 2 is illustrated in FIG. 2. Although FIG. 2 illustrates a right wrist band, it will be easy for those of ordinary skill in the art to fabricate a left wrist band.

To fabricate the band 2, a piece of elastic fabric material 3 is first cut. For example, the elastic fabric material from which the piece 3 is cut is the spongy, foamy elastic material of which are made the dry or wet suits currently used in water sports.

Figure 3:
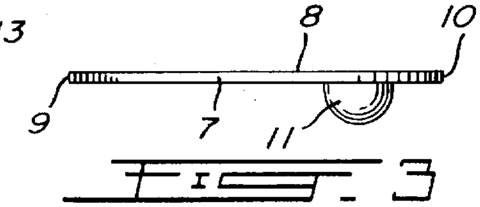
FIG. 3 is a side elevational view of a first embodiment of insert to be mounted in a pocket of the wrist band of FIG. 2, this insert being formed with the pressure-applying protuberance.
Figure 4:
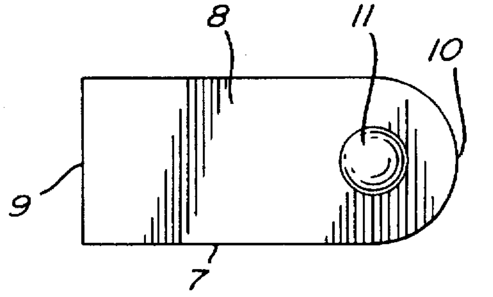
FIG. 4 is a bottom plan view of the insert of FIG. 3.

A patch 4 of leather or of any other suitable material is then stitched to the outer face of the central portion 5 of the piece 3 of elastic fabric material (see stitches 6) to form a pocket in which an insert 7 of high density foam material such as polyurethane or other suitable polymeric foam is placed. As shown in FIGS. 3 and 4, the insert 7 comprises a flat body 8 having the general outline of the pocket defined between the patch 4 and the piece 3 of elastic fabric material. More specifically, the flat body 8 is generally elongate and has a rectangular end 9 and a semicircular end 10. Formed on one side of the flat body 8 is a generally hemispherical protuberance 11 having a radius of approximately 5 mm. As illustrated in FIGS. 3 and 4, the protuberance 11 is situated at the semicircular end 10 of the flat body 8.

Referring back to FIG. 2, the central portion 5 of the piece 3 of elastic fabric material and therefore the pocket formed between the patch 4 and the piece 3 define a lateral rounded extension 13 of the wrist band 2. The protuberance 11 is located in the lateral extension 13 to apply a SMS to the area 1 (FIG. 1) when the elastic wrist band 2 is attached to the patient's wrist 24 as shown in FIG. 5.

As illustrated in FIG. 2, a tongue 15 formed of two superposed strips 16 and 17 is stitched to a first end 14 of the piece of elastic material 3. The outer strip 16 is made of leather or any other suitable material, while the inner strip 17 is made of VELCRO™ loop material. The tongue 15 is constructed by superposing the strips 16 and 17 and peripherally stitching these two strips together (see stitches 18). Upon stitching the strips 16 and 17 together, the first end 14 of the piece 3 of elastic fabric material is stitched between these layers 16 and 17 at the proximate end of the tongue 15.

As also illustrated in FIG. 2, a tongue 19 formed of two superposed strips 20 and 21 is stitched to a second end 22 of the piece of elastic fabric material 3. The outer strip 20 is made of VELCRO™ hook material, while the inner strip 21 is made of leather or any other suitable material. The tongue 19 is constructed by superposing the strips 20 and 21 and peripherally stitching these two strips together (see stitches 23). Upon stitching the strips 20 and 21 together, the second end 22 of the piece 3 of elastic fabric material is stitched between these strips 20 and 21 at the proximate end of the tongue 19.

In use, the wrist band 2 is placed around the user's wrist 24 and the inner VELCRO™ loop strip 17 is applied to the outer VELCRO™ hook strip 20 to thereby attach that band 2 to the user's wrist 24 (FIG. 5). If required, the wrist band 2 is then displaced to apply the protuberance 11 to the area 1 (FIG. 1) of the user's wrist 24.

To improve the user's comfort and for better aerating the user's skin, holes 25 and 26 are made in the piece 3 of elastic fabric material on the opposite sides of the leather patch 4.

When the activity of the user requires repetitive articulatory wrist movements of high amplitude, a lateral extension 27 of the piece 3 of elastic fabric material may be provided to better maintain the band 2 in place on the wrist 24 and therefore the protuberance 11 applied to the area 1. This extension 27 is cut integral with the piece 3, and is therefore made of the same elastic fabric material. Also, the extension 27 has a rounded free end 28 formed with a circular hole 29 in which the thumb 30 of the user's hand is inserted as shown in FIG. 5. The hole 25 is replaced by a plurality of smaller holes such as 31.

Also, as shown in FIG. 6, the insert 7 may comprise a plurality of generally hemispherical protuberances 32 smaller than and replacing the larger protuberance 11. The smaller protuberances 32 cover a larger surface than protuberance 11 to ensure that pressure is specifically applied to the area 1 through these generally hemispherical protuberances 32.

Figure 7:
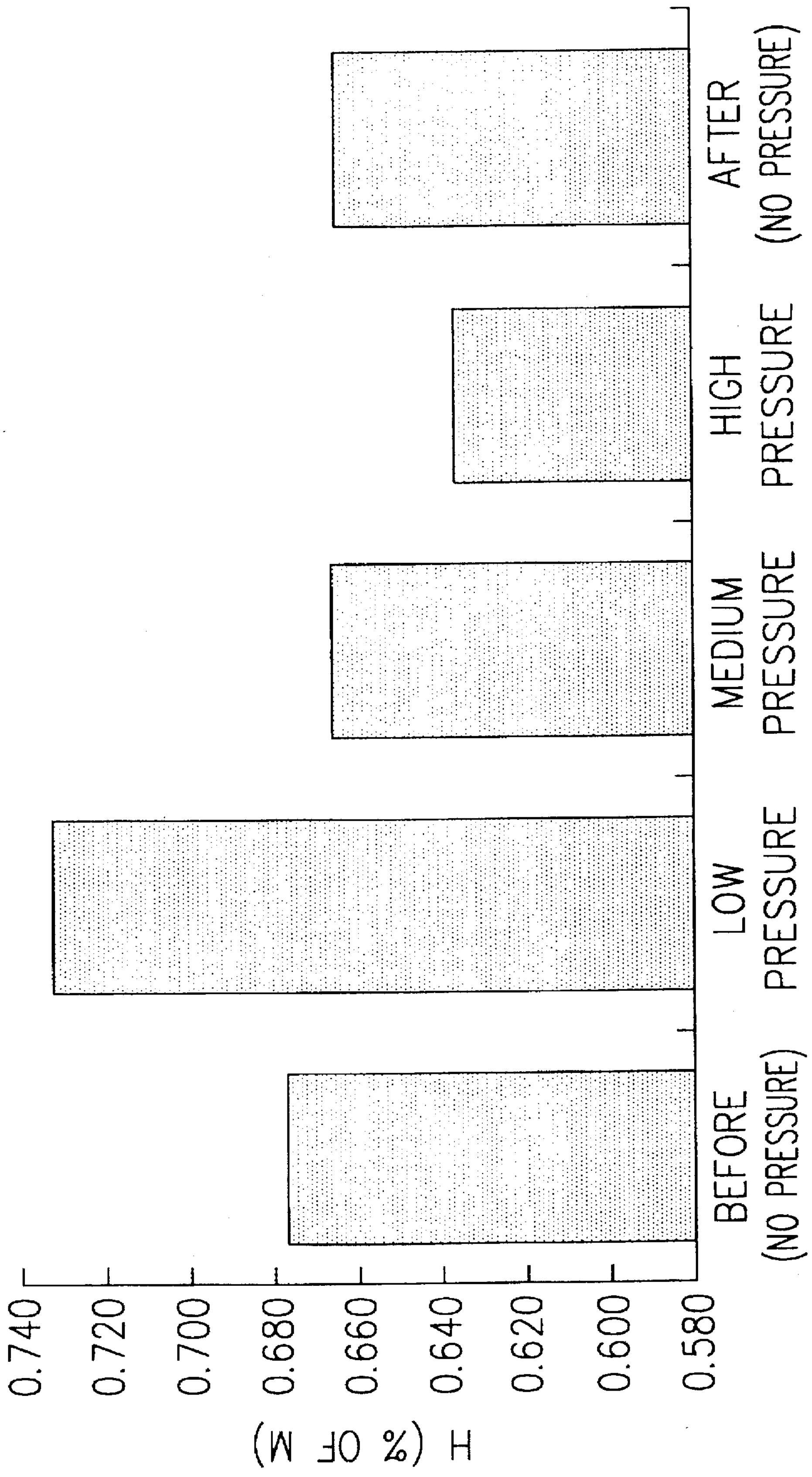
FIG. 7 is a graph of the reflex response H of a muscle or muscular group in function of the intensity of the external pressure applied to the mechano-receptors, the reflex response H being expressed as a percentage of the muscular response M.

It has been discovered experimentally, as illustrated by the graph of FIG. 7 that a low pressure (≦200 mmHg) stimulates only skin mechno-receptors (such as the Pacinian corpuscles) of the wrist joint to facilitate the reflex response of the muscular group of that joint, a medium pressure (>200 mmHg but <400 mmHg) has substantially no effect, and a high pressure (≧400 mmHg) stimulates the above mentioned skin mechano-receptors but also the deeper joint mechano-receptors (Golgi tendons) of the wrist joint to inhibit the reflex response (reduction of the reflex response) of the associated muscular group.

Therefore, a light cutaneous pressure (≦200 mmHg) stimulating only the skin mechano-receptors should be applied to the area 1 (FIG. 1) to facilitate the reflex response of the wrist's muscular group.

However, to rest or relax a given muscular group subjected, for example, to spasms, a high pressure (≧400 mmHg) stimulating the joint mechno-receptors (Golgi tendons) is applied to area 1 to inhibit the reflex response.

Pressure applied to the specific area 1 (FIG. 1) to produce a specific mechanical stimulation (SMS) is therefore sensed by the mechno-receptors of the wrist joint. These mechano-receptors decode the mechanical, pressure stimulus and transmits corresponding information to the central nervous system.

The information from the mechano-receptors is transmitted to many levels of the central nervous system. Mainly, the information from the mechno-receptors is transmitted to the spinal cord (or spinal marrow) and also to the brain. As the information is transmitted to the spinal cord, it influences the motor reflexes. Being transmitted to the brain it also influences central control of the wrist movements.

Research and experimentation have been conducted to explore the neurophysical effects of a specific mechanical stimulation (SMS). The results of these studies indicate that the effect of a light pressure (≦200 mmHg) SMS is to facilitate or to increase the contribution of the motor reflexes to the movements of the wrist. This facilitation of the reflex response causes an increase of the "spinal vigilance" itself increasing the muscular capacity without increasing the voluntary command from the brain.

Figure 1:
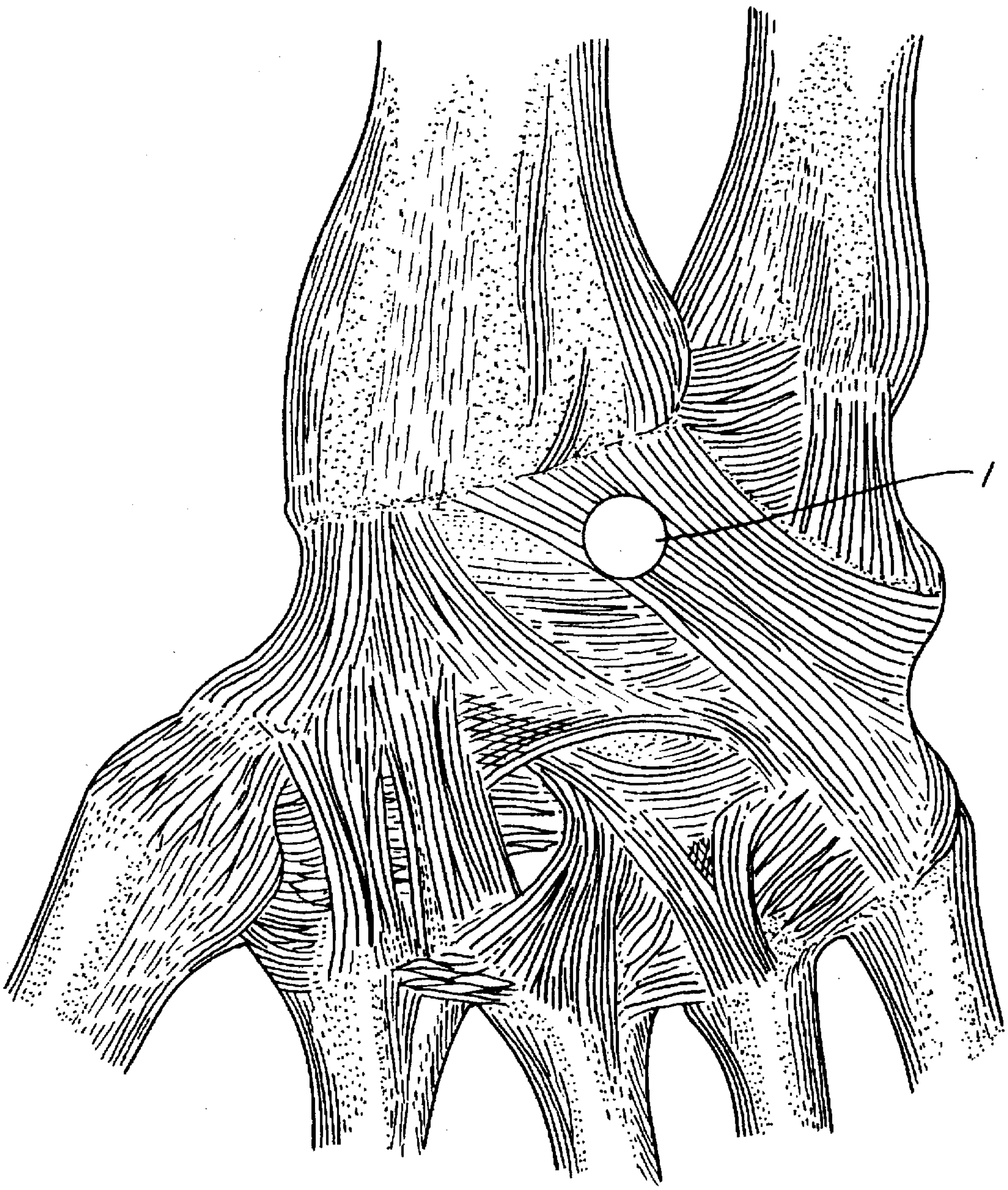
FIG. 1 is a schematic representation of the ligaments of the dorsal aspect of the left wrist.
Figure 8:
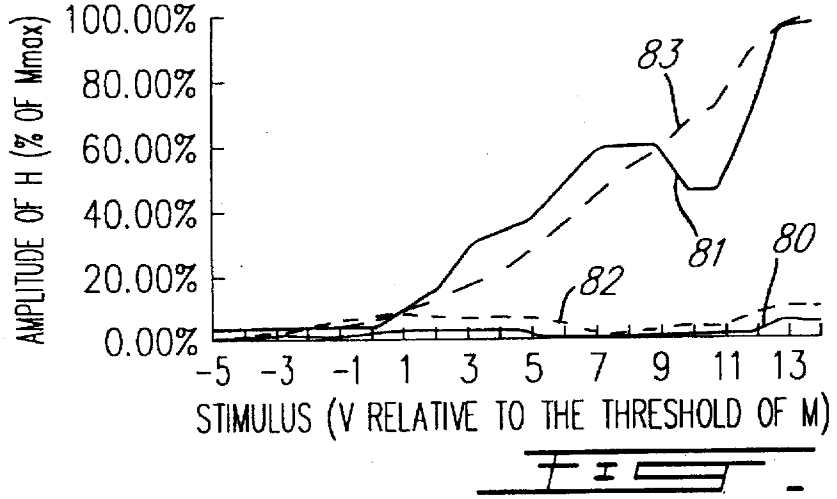
FIG. 8 is a graph of the amplitude of the reflex response H of the wrist's muscular group in function of an external stimulus V with and without application of a pressure (SMS) to the mechno-receptors, the amplitude of the reflex response H being expressed as a percentage of the maximum muscular response $M_{max}$, and the external stimulus being expressed relative to the threshold of the muscular response M.

Experimentation has demonstrated that application of a light pressure (≦200 mmHg) to the area 1 of FIG. 1 facilitates the reflex response by approximately 16.1%, as evidenced by the graph of FIG. 8. In this graph, curve 80 represents the amplitude of the reflex response H of the wrist's muscular group in function of the external stimulus V without application of a pressure (SMS) to the mechano-receptors, curve 81 represents the amplitude of the muscular response M of the wrist in function of the external stimulus V without application of a SMS to the mechano-receptors, curve 82 represents the amplitude of the reflex response H of the wrist's muscular group in function of the external stimulus V with the application of a pressure (SMS) to the mechano-receptors, and curve 83 represents the amplitude of the muscular response M of the wrist in function of the external stimulus V with the application of a SMS to the mechano-receptors. The graph of FIG. 8 therefore indicates that the light pressure increases the capacity and facility of the muscle(s) to respond to an external stimulus. This could be explained by the solicitation of the skin mechano-receptors in response to the pressure stimulus.

Figure 9:
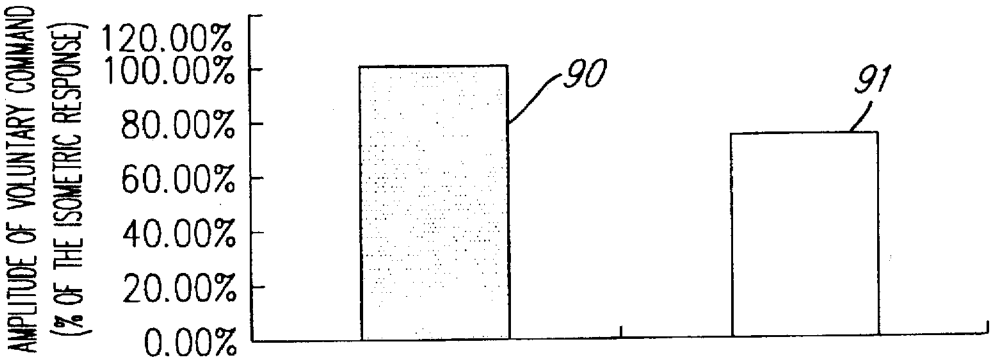
FIG. 9 is a graph of the amplitude of the voluntary command with and without application of a pressure (SMS) to the mechano-receptors of the wrist's muscular group, the amplitude of the voluntary command being expressed as a percentage of the isometric response.

Also, a SMS (light pressure ≦200 mmHg) applied to the area 1 of FIG. 1 causes a reduction of the nervous activity associated to the maximal contraction. More specifically, the voluntary command from the brain to reach maximal contraction is reduced by approximately 25% as demonstrated by the graph of FIG. 9. In this graph, curve 90 corresponds to the amplitude of the voluntary command without application of a SMS to the mechano-receptors, and curve 91 corresponds to the amplitude of the voluntary command with the application of a pressure (SMS) to the mechano-receptors.

Figure 10:
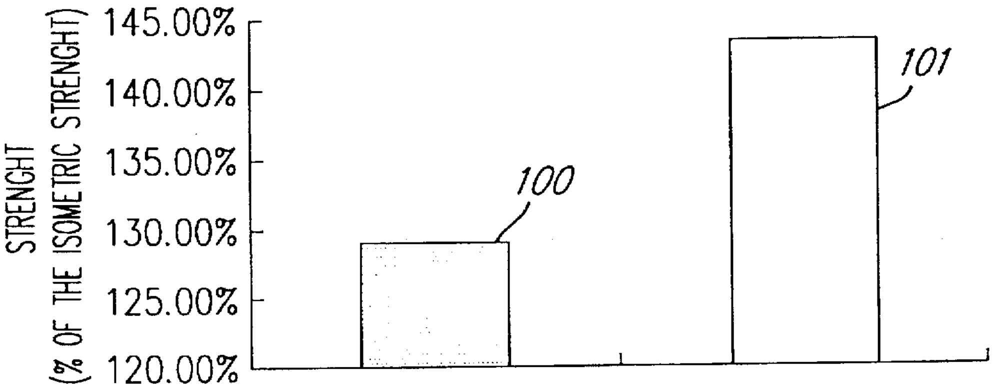
FIG. 10 is a graph of the strength of the wrist's muscular group with and without application of a pressure (SMS) to the mechno-receptors, this strength being expressed as a percentage of the isometric strength.

Finally, the graph of FIG. 10 demonstrates that the increase of the reflex response along with the reduction of the voluntary command result into an increase of the maximal strength by 11%. The increase in strength was generally associated with an increase in EMG level. In the graph of FIG. 10, curve 100 corresponds to the strength without application of a SMS to the mechno-receptors, and curve 101 corresponds to the strength with the application of a pressure (SMS) to the mechano-receptors.

Therefore, according to the above experimental results, a light pressure (≦200 mmHg) SMS increases the reflex response, reduces the voluntary nervous command and increases the strength. These results strongly suggest that the increase of muscular capacity expressed by the maximal strength is directly connected to the increase of the reflex response. This increase of the reflex response accordingly increases the "spinal vigilance" so as to increase the strength while reducing the activity at the level of the central nervous system.

Therefore, a light pressure SMS causes an increase of the muscular capacity by means of a natural reflex mechanism guided by the mechno-receptors involved. For the same work, the relative effort of the muscular system will seem weaker since the capacity is increased. This apparent reduction of the relative effort enables prevention of functional problems such as carpal tunnels, tendinitis, etc. often related to the use of computer keyboards or mice.

A light pressure SMS therefore increases the functional capacity, i.e. the capacity to produce a force by at least 10%. This increase of muscular capacity reduces overload by rendering work easier whereby a SMS could be used to protect the joint (wrist) and prevent overuse or misuse injuries associated to repetitive motion. It also reduces the risks of repetitive motion syndromes generally caused by overuse of equipments and repetitive uninterrupted working activities.

It should be pointed out here that the mechano-receptors are sensitive to a SMS upon movement of the joint (wrist) and this sensitivity increases proportionally with the amplitude of the movement whereby an automatic compensation of the action of the SMS in function of the amplitude of movement is carried out.

Experimentation was also conducted on the ankle joint of many human subjects. More specifically, university students were tested on a Kincom dynamometer for maximum isometric and concentric force (30°/sec, 3 trials) of four ankle movements, namely pronation, supination, flexion and extension, and that for two conditions: with and without specific mechanical stimulation (SMS).

Figure 11:
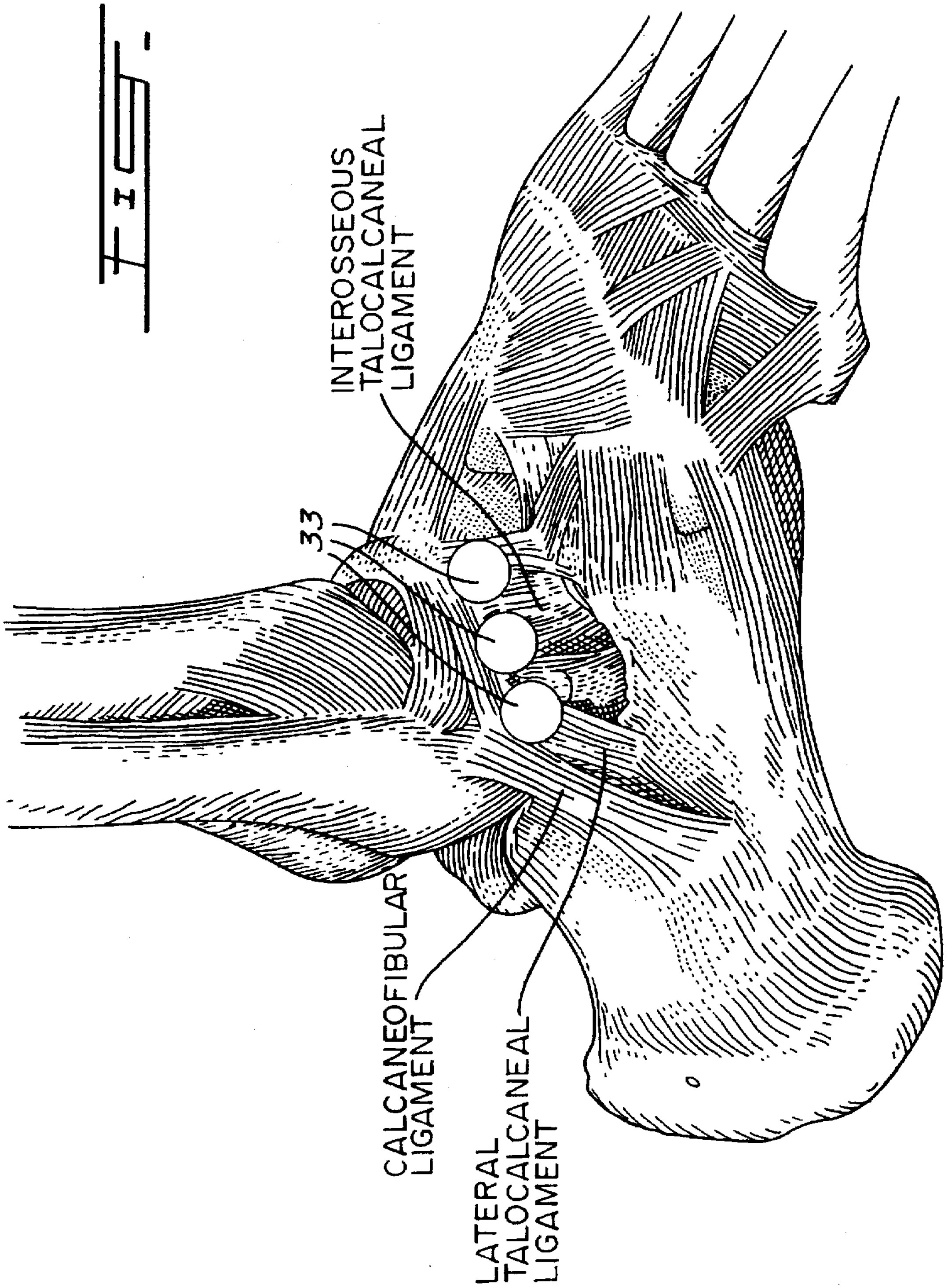
FIG. 11 is a schematic representation of the ligaments of a human ankle joint.

Specific mechanical stimulation (SMS) was applied in the form of a light pressure on the talocalcaneal region of the ankle, more specifically in the region of the calcaneofibular ligament, lateral talocalcaneal ligament and interosseous talocalcaneal ligament. Referring to FIG. 11, pressure was applied to the area 33 of the subjects' ankle by means of a piece of high density foam material maintained over the area 33 of interest through an elastic ankle band.

An example of elastic ankle band 34 is illustrated in FIG. 12. It will appear to those of ordinary skill in the art that the elastic ankle band 34 of FIG. 12 fits on both the left and right ankles.

To fabricate the band 34, a piece 35 of elastic fabric material is first cut. For example, the elastic fabric material from which the piece 35 is cut is the foamy elastic material of which are made the dry or wet suits currently used in water sports.

The piece 35 of elastic fabric material is generally ovoid and formed with a generally central circular hole 36. The piece 35 of elastic fabric material is also provided with two opposite extensions 37 and 38.

An elongate piece 39 of leather or of any other suitable material has its proximate end 40 stitched to the outer face of the extension 38 (see stitches 41) to form a pocket in which an insert 42 of high density foam material such as polyurethane or other suitable polymeric foam is placed. As shown in FIGS. 14 and 15, the insert 42 comprises a flat body 43 having the general outline of the pocket defined between the piece 39 of leather and the extension 38. Formed on one side of the flat body 43 is a series of three generally hemispherical protuberances 44–46 each having a radius of approximately 5 mm. Of course, the protuberances 44–46 are turned toward the ankle when the insert 42 is mounted in the pocket between the piece 39 of leather and the extension 38, to apply a SMS to the area 33 (FIG. 11) when the elastic ankle band 34 is attached to the patient's ankle 47 as shown in FIG. 13.

A strip 53 of VELCRO™ hook material is stitched to the outer face of the elongate piece 39 of leather, between the extension 38 and the free end of the elongate piece 39.

As illustrated in FIG. 12, a tongue 48 formed of two superposed strips 49 and 50 is stitched to the free end 51 of the extension 37 of the piece 35 of elastic material. The outer strip 49 is made of leather or any other suitable material, while the inner strip 50 is made of VELCRO™ loop material. The tongue 48 is constructed by superposing the strips 49 and 50 and peripherally stitching these two strips together (see stitches 52). Upon stitching the strips 49 and 50 together, the free end 51 of the piece 35 of elastic fabric material is stitched between these strips 49 and 50 at the proximate end of the tongue 48.

Figure 13A:
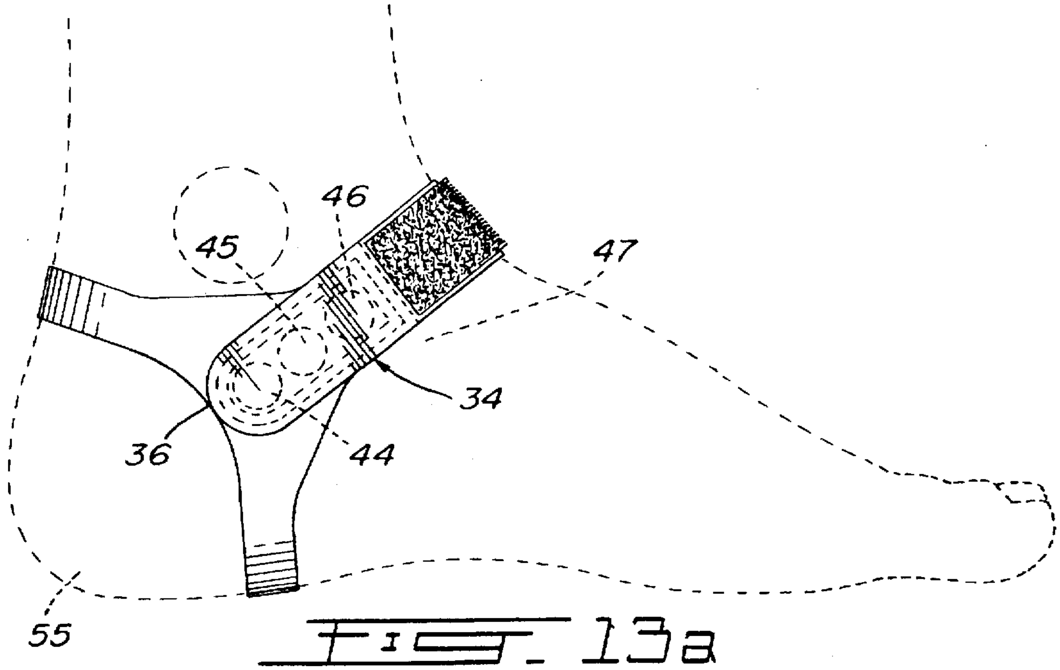
FIG. 13*a* is an outside, side elevational view of a human ankle wearing the elastic ankle band of FIG. 12.

In use, the elastic ankle band 34 is placed around the user's ankle 47. More specifically, the user places his heel 55 (FIG. 13*a*) in the hole 36 of the piece 35 of elastic fabric material. Then, the inner VELCRO™ loop strip 50 is applied to the outer VELCRO™ hook strip 53 to thereby attach the band 34 to the user's ankle 47 as illustrated in FIG. 13. If required, the ankle band 34 is then displaced to apply the series of protuberances 44–46 to the area 33 (FIG. 1) of the user's ankle 47.

Figure 13B:
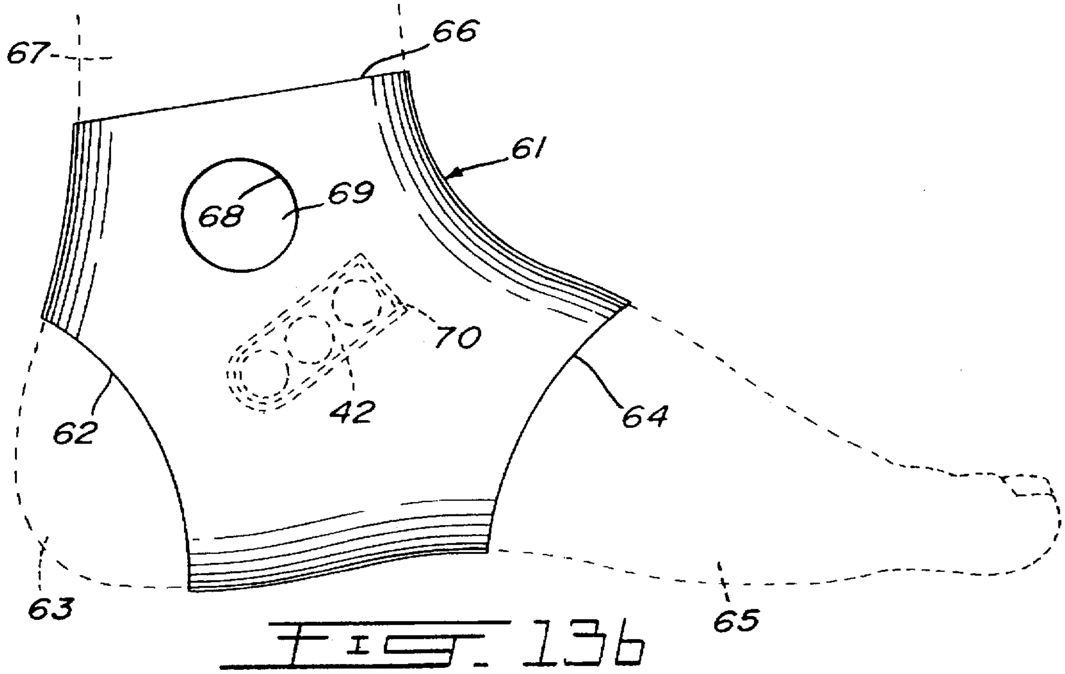
FIG. 13*b* is an outside, side elevational view of a human ankle wearing a sock-like elastic ankle band.

FIG. 13*b* illustrates another possible embodiment of elastic ankle band 61. The ankle band 61 has the configuration of a portion of sock formed with an opening 62 for the user's heel 63, an opening 64 for the user's foot 65, an opening 66 for the user's leg 67 and an opening such as 68 for each malleolus 69 of the user.

Again, the ankle band 61 is made for example of the foamy elastic fabric material of which are made the dry or wet suits currently used in water sports.

The sock-like elastic ankle band 61 is formed with a pocket 70 to receive an insert such as 42 made of high density foam material and formed with a series of three generally hemispherical protuberances for applying a SMS to the area 33 (FIG. 11) when the sock-like ankle band 61 is placed on the patient's ankle as shown in FIG. 13*b*.

Again, it has been discovered experimentally, as illustrated by the graph of FIG. 7 that a low pressure (≦200 mmHg) stimulates only skin mechano-receptors (such as the Pacinian corpuscles) of the ankle joint to facilitate the reflex response of the muscular group of that joint, a medium pressure (>200 mmHg but <400 mmHg) has substantially no effect, and a high pressure (≧400 mmHg) stimulates the above mentioned skin mechno-receptors but also the deeper mechano-receptors (Golgi tendons) of the wrist joint to inhibit the reflex response (reduction of the reflex response) of the associated muscular group.

Therefore, a light cutaneous pressure (≦200 mmHg) stimulating only the skin mechano-receptors should be applied to the area 33 (FIG. 11) to facilitate the reflex response of the associated muscular group.

However, to rest or relax that muscular group subjected, for example, to spasms, a high pressure (≧400 mmHg) stimulating the joint mechno-receptors (Golgi tendon) is applied to areas 33 to inhibit the reflex response.

Pressure applied to the specific area 33 (FIG. 11) to produce a specific mechanical stimulation (SMS) is therefore sensed by the mechno-receptors of the ankle joint. These mechano-receptors decode the mechanical, pressure stimulus and transmits corresponding information to the central nervous system.

The information from the mechano-receptors is transmitted to many levels of the central nervous system. Mainly, the information from the mechano-receptors is transmitted to the spinal cord (or spinal marrow) and also to the brain. As the information is transmitted to the spinal cord, it influences the motor reflexes. Being transmitted to the brain it also influences central control of the ankle movements.

Research and experimentation have been conducted to explore the neurophysical effects of a specific mechanical stimulation (SMS). The results of these studies indicate that the effect of a light pressure (≦200 mmHg) SMS is to facilitate or to increase the contribution of the motor reflexes to the movements of the ankle. This facilitation of the reflex response causes an increase of the "spinal vigilance" itself increasing the muscular capacity without increasing the voluntary command from the brain.

Figure 16:
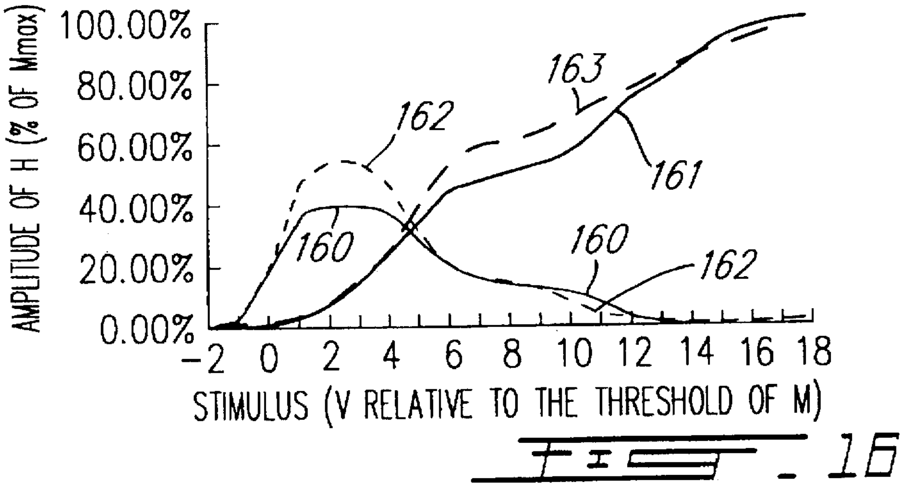
FIG. 16 is a graph of the amplitude of the reflex response H of the ankle's muscular group in function of an external stimulus V with and without application of a pressure (SMS) to the mechno-receptors, the amplitude of the reflex response H being expressed as a percentage of the maximum muscular response $M_{max}$, and the external stimulus being expressed relative to the threshold of the muscular response M.

Experimentation has demonstrated that application of a light pressure (≦200 mmHg) to the areas 33 of FIG. 1 facilitates the reflex response of the ankle joint by approximately 37%, as evidenced by the graph of FIG. 16. In this graph, curve 160 represents the amplitude of the reflex response H of the ankle's muscular group in function of the external stimulus V without application of a pressure (SMS) to the mechano-receptors, curve 161 represents the amplitude of the muscular response M of the ankle in function of the external stimulus V without application of a SMS to the mechano-receptors, curve 162 represents the amplitude of the reflex response H of the ankle's muscular group in function of the external stimulus V with the application of a pressure (SMS) to the mechano-receptors, and curve 163 represents the amplitude of the muscular response M of the ankle in function of the external stimulus V with the application of a SMS to the mechano-receptors. The graph of FIG. 16 therefore indicates that the light pressure increases the capacity and facility of the muscle(s) to respond to an external stimulus. This could be explained by the solicitation of the skin mechano-receptors in response to the pressure stimulus.

Figure 17:
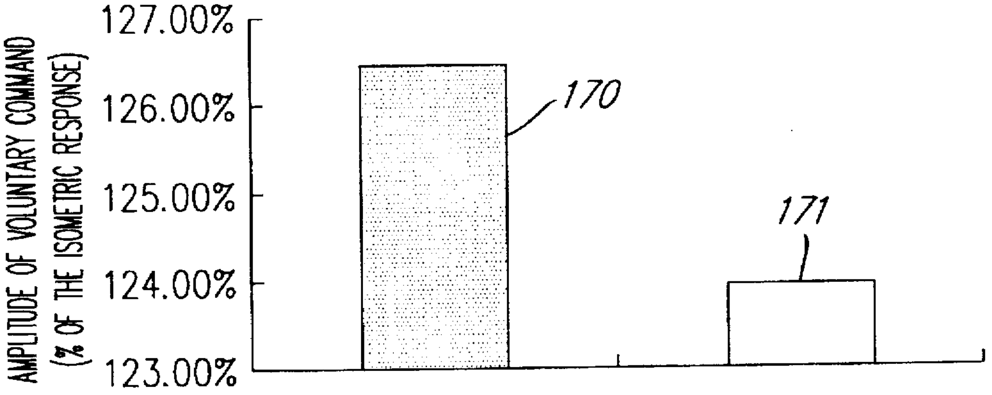
FIG. 17 is a graph of the amplitude of the voluntary command with and without application of a pressure (SMS) to the mechano-receptors of the ankle's muscular group, the amplitude of the voluntary command being expressed as a percentage of the isometric response.

Also, a SMS (light pressure ≦200 mmHg) applied to the areas 33 of FIG. 11 causes a reduction of the nervous activity associated to the maximal contraction. More specifically, the voluntary command from the brain to reach maximal contraction is reduced by approximately 2% as demonstrated by the graph of FIG. 17. In this graph, curve 170 corresponds to the amplitude of the voluntary command without application of a SMS to the mechano-receptors, and curve 171 corresponds to the amplitude of the voluntary command with the application of a pressure (SMS) to the mechano-receptors.

Figure 18:
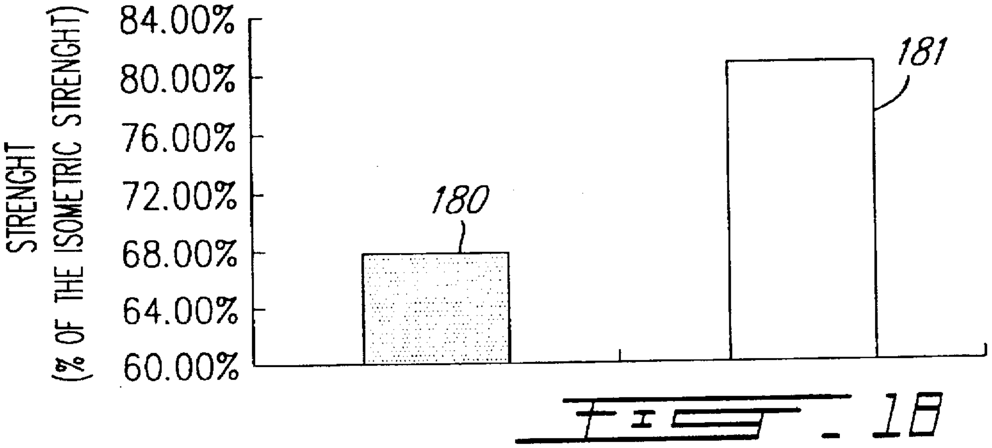
FIG. 18 is a graph of the strength of the ankle's muscular group with and without application of a pressure (SMS) to the mechno-receptors, this strength being expressed as a percentage of the isometric strength.

Finally, the graph of FIG. 18 demonstrates that the increase of the reflex response along with the reduction of the voluntary command result into an increase of the maximal strength by 19%. In the graph of FIG. 18, curve 180 corresponds to the strength of the ankle's muscular group without application of a SMS to the mechano-receptors, and curve 181 corresponds to the strength with the application of a pressure (SMS) to the mechno-receptors.

Again, the mechano-receptors are sensitive to a SMS upon movement of the joint (ankle) and this sensitivity increases proportionally with the amplitude of the movement whereby an automatic compensation of the action of the SMS in function of the amplitude of movement is carried out.

Figure 19:
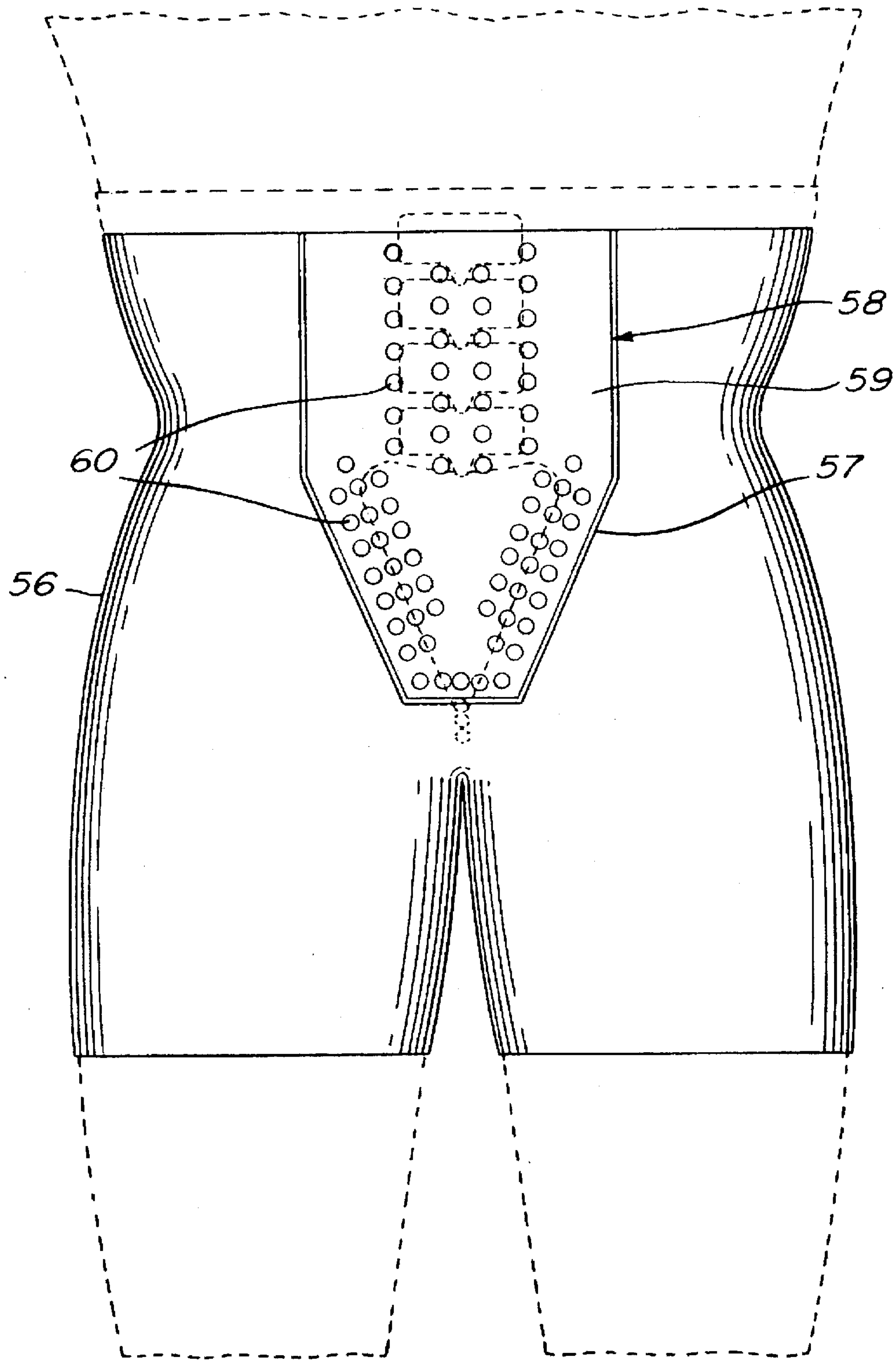
FIG. 19 is a rear elevational view of extensible cyclist shorts having a rear pocket to receive an insert comprising a flat body formed on one side with numerous protuberances to apply a pressure (SMS) in the region of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, piriformis ligaments.

As illustrated in FIG. 19, the same concept can be applied to the lumbar spine.

In that particular case, extensible cyclist shorts 56 are provided with a rear pocket 57 to receive an insert 58. Pocket 57 is formed by sewing an additional inside layer of extensible fabric material to the extensible shorts 56.

The insert 58 is made of high density foam material such as polyurethane or other suitable polymeric foam and comprises a flat body 59 on one side of which are formed numerous protuberances such as 60 to apply a light pressure SMS in the region of the intraspinalis muscles, intraspinalis ligaments, intratransverse muscles, intratransverse ligaments, semispinalis muscles, semispinalis ligaments, sacrospinalis muscles, sacrospinalis ligaments, iliopsoas muscles, iliopsoas ligaments, piriformis muscles, piriformis ligaments.

The effect of a light pressure SMS on the muscular group associated to the lumbar spine is similar to what has been described hereinabove in relation to the wrist and ankle joints.

Of course, it is within the scope of the present invention to use the concept according to the present invention with body joints other than the wrist, ankle and lumbar spine. Also, the concept according to the present invention can be applied to a single muscle instead of a muscular group.

Although the present invention has been described hereinabove with reference to a preferred embodiment thereof, this embodiment can be modified at will, within the scope of the appended claims, without departing from the spirit and nature of the subject invention.

What is claimed is:

1. A method of facilitating the reflex response of a muscle or muscular group articulating a wrist joint of a living body, the living body comprising skin mechano-receptors guiding a natural reflex mechanism of said muscle or muscular group, said method comprising the steps of:

mounting a pressure-applying member on the living body directly over the dorsal radiocarpal ligament; and lightly applying the pressure-applying member to the living body directly over the dorsal radiocarpal ligament and maintaining the pressure-applying member lightly applied to said body to thereby apply to the skin mechano-receptors an external pressure having an intensity<200 mmHg for facilitating the reflex response of the muscle or muscular group.

2. A method of inhibiting the reflex response of a muscle or muscular group articulating a wrist joint of a living body, the living body comprising joint mechano-receptors guiding a natural reflex mechanism of said muscle or muscular group, said method comprising the steps of:

mounting a pressure-applying member on the living body directly over the dorsal radiocarpal ligament; and firmly applying the pressure-applying member to the living body directly over the dorsal radiocarpal ligament and maintaining the pressure-applying member firmly applied to said body to thereby apply to the joint mechano-receptors an external pressure having an intensity≧400 mmHg for inhibiting the reflex response of the muscle or muscular group.

* * * * *